(12) United States Patent
Cohen

(10) Patent No.: US 6,488,156 B1
(45) Date of Patent: Dec. 3, 2002

(54) METHOD AND SYSTEM FOR VERIFICATION OF FERTILIZATION OF POULTRY EGGS

(76) Inventor: Michael Cohen, Kfar Etzion, Post North, Yehuda 90912 (IL)

(*) Notice: Subject to any disclaimer, the term of this patent is extended or adjusted under 35 U.S.C. 154(b) by 0 days.

(21) Appl. No.: 09/488,698

(22) Filed: Jan. 20, 2000

(30) Foreign Application Priority Data

Jan. 20, 1999 (IL) .............................. 128.157

(51) Int. Cl.$^7$ .................. A01K 43/04; A01K 45/00; A01K 43/00
(52) U.S. Cl. .................. 209/510; 209/511; 209/936; 356/52; 324/71.1
(58) Field of Search ................. 209/510, 511, 209/936; 356/52; 324/71.1; 435/806

(56) References Cited

U.S. PATENT DOCUMENTS

| 2,636,925 | A |   | 4/1953  | Gascoigne |
|-----------|---|---|---------|-----------|
| 3,533,504 | A | * | 10/1970 | Bures ......................... 209/510 |
| 3,540,824 | A | * | 11/1970 | Fonda ......................... 209/511 |
| 4,955,728 | A | * | 9/1990  | Hebrank ....................... 209/511 |
| 5,615,777 | A | * | 4/1997  | Weichman et al. .......... 209/511 |
| 6,149,956 | A | * | 11/2000 | Boerjan ....................... 426/231 |
| 6,244,214 | B1| * | 6/2001  | Hebrank ....................... 119/6.8 |

FOREIGN PATENT DOCUMENTS

| JP | 09127096       | 5/1997 |
| WO | WO 00/01302 A1 | 1/2000 |

* cited by examiner

Primary Examiner—Donald P. Walsh
Assistant Examiner—Daniel K Schlak
(74) Attorney, Agent, or Firm—Flehr Hohbach Test Albritton & Herbert LLP

(57) ABSTRACT

A method for verification of the presence of a living embryo in an incubating poultry egg. The method comprises the steps of: causing at least two electrodes to make conductive contact with the outside surface of the shell of an egg; amplifying any of the analog signals received via two of the at least two electrodes; analyzing the signals after amplification, using a program in a microprocessor, to establish whether the signals originated in the cardiac activity of the embryo; and providing information confirming or negating the presence of a living embryo in the egg. The invention also provides a corresponding system for carrying out the method.

18 Claims, 5 Drawing Sheets

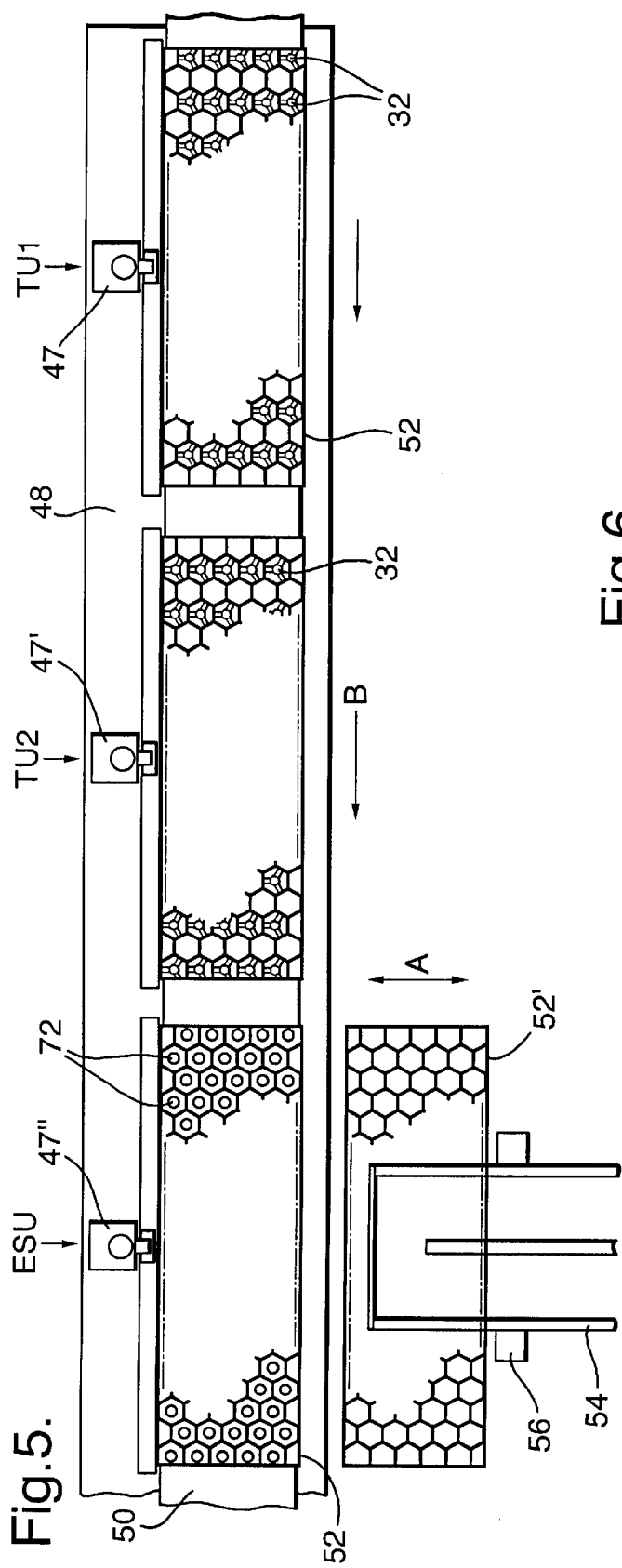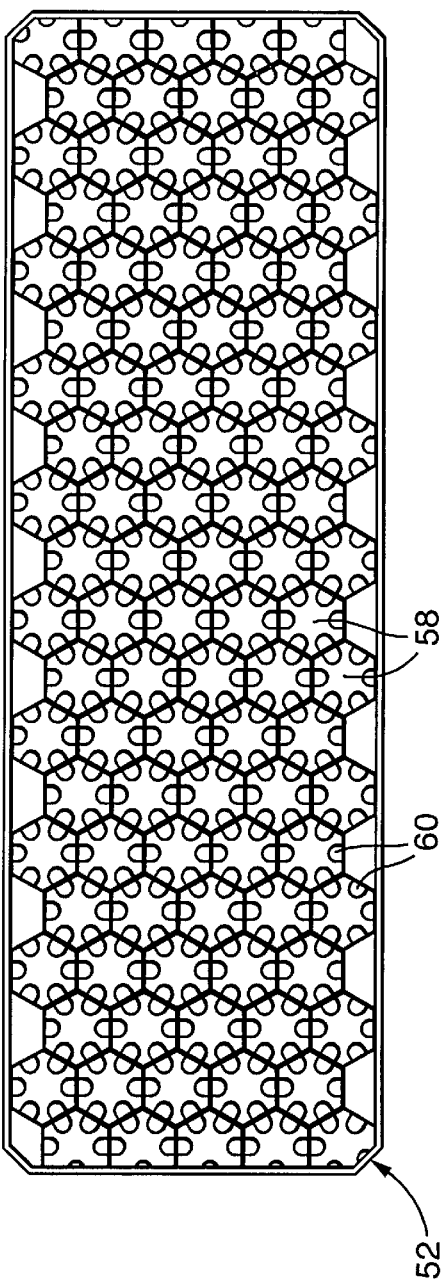

METHOD AND SYSTEM FOR VERIFICATION OF FERTILIZATION OF POULTRY EGGS

FIELD OF THE INVENTION

The present invention relates to a method and a system for verification of the presence of living poultry embryos in incubating poultry eggs.

BACKGROUND OF THE INVENTION

About 10% of all eggs reaching chick hatcheries are non-fertile. For both economic and hygienic reasons, the hatcheries are interested in eliminating these eggs at the earliest possible opportunity. The conventional process used to this end is known as "candling". In this process, on about the 10th day of incubation, an experienced operator in a darkened room manually passes a strong light source from egg to egg and looks for a network of tiny blood vessels in each now translucent egg. This network indicates a developing embryo. Eggs lacking this network are immediately discarded, as they obviously will not end up as chicks and, at this stage, are no longer fit for human consumption.

The time-honored method of candling has several serious disadvantages. It requires trained manpower (large hatcheries incubate tens of thousands of eggs at any given time), yet even the most experienced operators will fail to correctly diagnose one out of every ten eggs. The operators will either fail to recognize the capillaries or they will pass as fertile an egg in which the capillaries are still discernible, thus giving the appearance of a properly broodable egg, when in fact the embryo has died.

In recent years, attempts have been made to increase the low efficiency and reduce the high demands for operator skill of the candling process by introducing devices built around optical systems that, to some extent, could also be automated. Yet while these improved candling devices could, with some reliability, differentiate between fertilized and non-fertilized chicken eggs, they fail to distinguish between fertilized eggs containing a live embryo and eggs which, although still displaying the capillaries, contain embryos that have died. Furthermore, these optical devices are altogether unsuitable for checking turkey eggs which have shells that are thicker and far less translucent than those of chicken eggs.

SUMMARY OF THE INVENTION

It is thus one of the objects of the present invention to provide a method for verification of the presence of living poultry embryos in incubating eggs. This method is not based on the expertise of human operators, has a much smaller error margin, and can be largely automated.

It is a further object of the present invention to provide a method that will pick out for discarding not only non-fertilized eggs, but also originally fertilized eggs in which the embryo has died.

It is a still further object of the invention to provide a method for handling turkey eggs which have shells that are much thicker and far less translucent than those of chicken eggs.

These objectives are achieved by providing a method according to the present invention for verification of the presence of a living embryo in an incubating poultry egg. This method comprises the steps of: causing at least two electrodes to make conductive contact with the outside surface of the shell of said egg; amplifying any of the analog signals received via two of the at least two electrodes; analyzing the signals after amplification, using a program in a microprocessor, to establish whether the signals originated in the cardiac activity of the embryo; and providing information confirming or negating the presence of a living embryo in the egg.

A system is also provided according to the present invention for verification of the presence of a living embryo in incubating poultry eggs. The system comprises: an array of detector heads, each provided with at least two electrodes adapted to make contact with the surface of the shell of one of the eggs; a microprocessor responsive to signals received by the electrodes and adapted to establish the presence or absence of signals originating in the cardiac activity of a living embryo; and means controlled by said microprocessor to facilitate separation of the eggs found lacking such a presence from those in which such a presence has been confirmed.

The invention is based on the fact that the cardiac activity of the embryo produces characteristic electrical signals as early as at the end of the third day of incubation. By amplifying these signals, picked up by non-invasive electrodes that leave the eggshell intact, and analyzing them after separating them from the inevitable noise superposed on them, proof can be obtained not only that the egg has been fertilized, but also that it contains a live embryo. Conversely, the absence of such signals signifies a non-fertilized egg or a dead embryo in an originally fertilized egg.

BRIEF DESCRIPTION OF THE DRAWINGS

The invention will now be described in connection with certain preferred embodiments with reference to the following illustrative figures so that it may be more fully understood.

FIG. 5 is a schematic top view of the work station of the system according to the invention;

FIG. 6 is a top view of the egg tray used by the system;

DETAILED DESCRIPTION OF PREFERRED EMBODIMENTS

With specific reference now to the figures, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Figure 1:
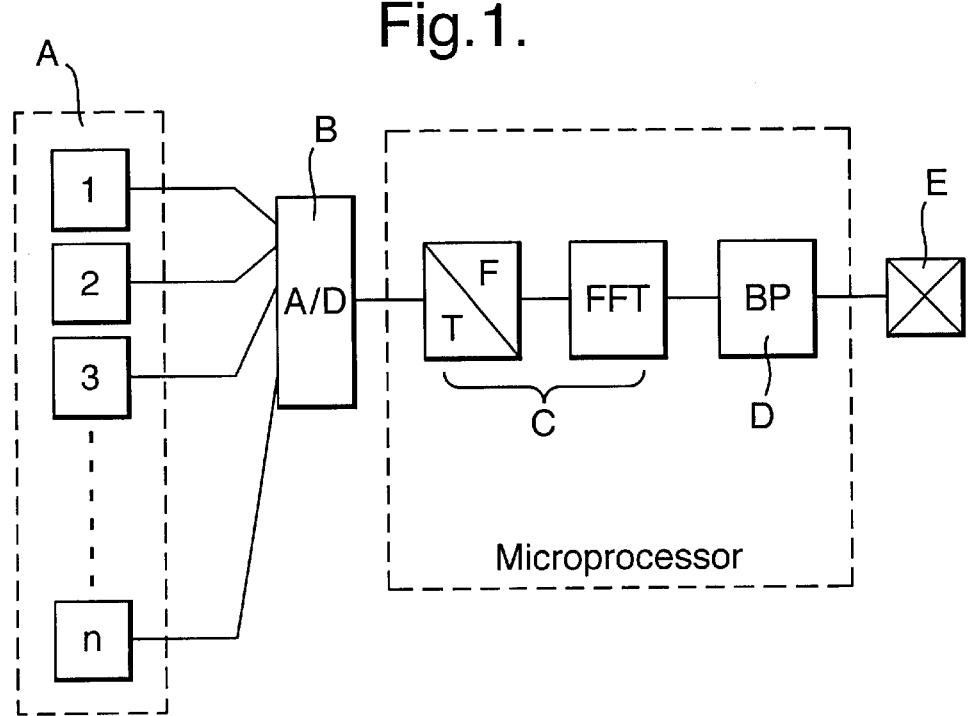
FIG. 1 is a general block diagram of the method according to the present invention.

Referring now to FIG. 1, there is shown a data acquisition block 100 comprising a plurality of n detector heads 101 provided with electrodes that can be brought into contact with the eggs to be tested. The actual configuration of the detector heads will be shown and explained further below.

Figure 2:
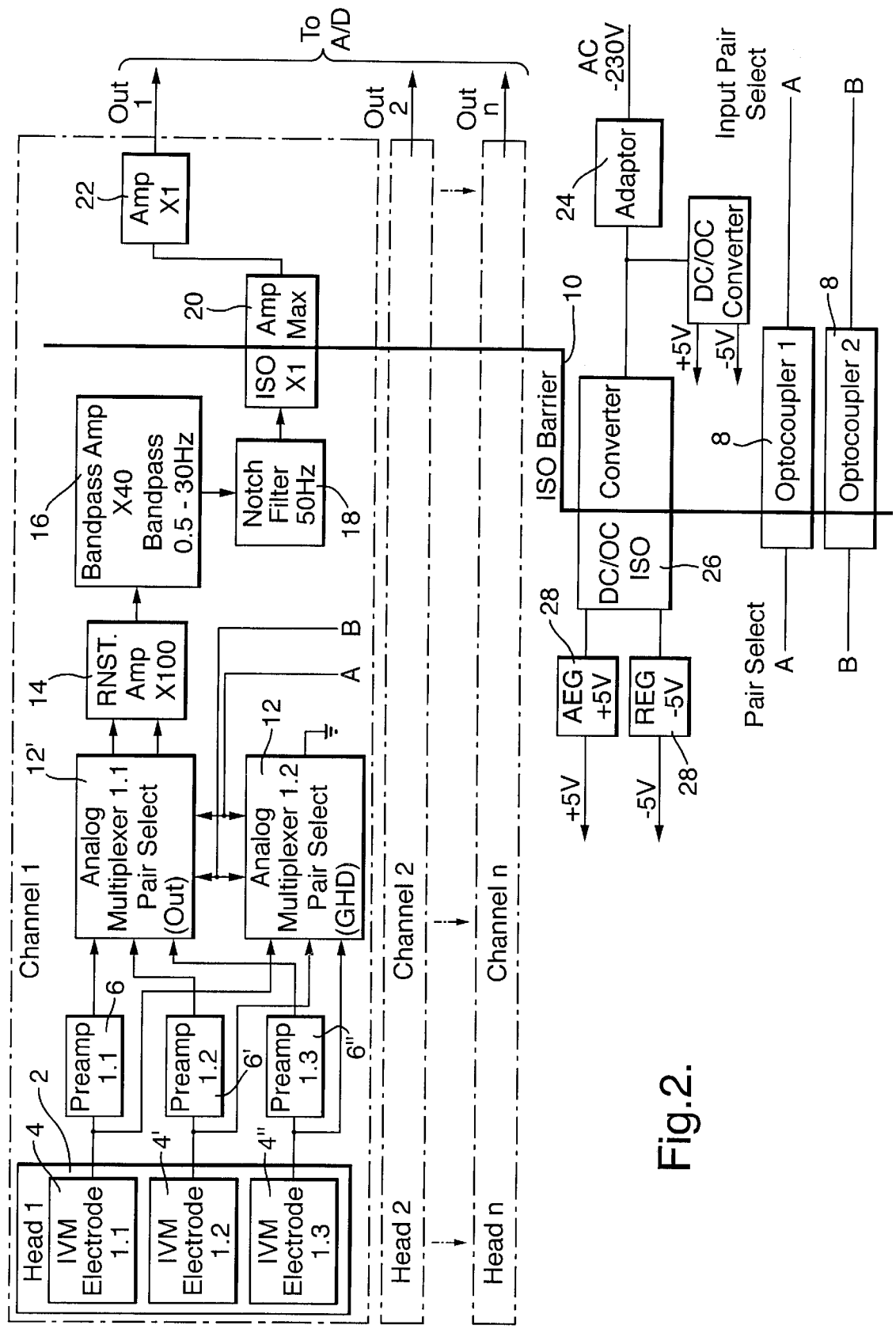
FIG. 2 is a more detailed flow diagram illustrating the method according to the invention.

Each electrode of a detector head 101 is provided with its own preamplifier. All of the electronic components belonging to block 100, and shown in greater detail in FIG. 2, are accommodated within a Faraday-cage type space to reduce noise, i.e., to improve the signal-to-noise ratio.

An analog-to-digital (A/D) conversion block 102 in the present embodiment uses an ADLINK A/D card. Block 102 is the connecting link to a microprocessor 103.

Blocks 104 and 105 of the microprocessor 103 are controlled by dedicated software. Block 104 performs a fast Fourier transform, determining the frequency domain and calculating the signal spectrum. Block 105 performs the required analysis. Experience has shown the pulse of an embryo of 20 days to be about 3 Hz. A bandpass filter of 2 Hz–4 Hz is advantageously used, with the spectrum power being calculated within this range.

A monitor 106 graphically indicates those eggs in a tray (see FIG. 5) that are to be discarded, being either non-fertilized or containing a dead embryo.

FIG. 2 shows a plurality of n channels. Only channel 1 is fully detailed, it being understood that channels 2-n are identical to channel 1. Each channel comprises one detector head 101, to be fully described further below. Each head is provided with three electrodes 107, 107', 107", the characteristic properties of which will be explained in conjunction with the description of the detector heads.

The electrodes 107, 107', 107" are provided with their own preamplifiers 108, 108', 108", respectively. This serves to overcome the ohmic resistance of the egg shell, estimated to be of an order of magnitude of several MΩ, to facilitate the transfer of the primary signal to the next amplifier, using standard wire leads.

Although the acquisition of a signal indicating the cardiac activity of the embryo can be effected by means of only two electrodes (of which one is grounded), the present invention uses the three electrodes 107, 107', 107" because of the fact that the strength of the signal obtained is clearly affected by the distance of the electrodes from the embryonic heart. Now, since the latter is scarcely ever located precisely on the longitudinal axis of the egg, straight lines from the points of contact of diametrically opposite electrodes to the embryonic heart would rarely, if ever, constitute the optimum, i.e., shortest, path. For this reason, the present invention provides the three electrodes 107, 107', 107", angularly spaced apart by 120° (see FIG. 4), from which, by permutational signal sampling, that pair of electrodes is selected which yields the strongest signals. This selection is controlled by the microprocessor 103 of FIG. 1 through leads 109, 109' via optocouplers 110 and effected by analog multiplexers 111, 111', which act as electronic switches. Multiplexer 111 switches between the grounded (reference) electrodes and multiplexer 111' switches between the non-grounded output electrodes.

The signal from the selected pair of the electrodes 107, 107', 107" is fed to an instrument amplifier 113, where it is amplified, e.g., x 100. It is then fed to a bandpass amplifier 114 for amplification, e.g., x 40, of the signal and filtering out of frequencies lower than 0.5 Hz and higher than 30 Hz, which are not required for the purpose of the system.

Further processing of the signal is performed by a notch filter 115. This filter filters out the 50 Hz noise produced by the 220 V A.C. mains.

The signal leaves the Faraday-cage environment via an ISO amplifier 116. This amplifier cleans the signal of wireless noise before it is fed to a final amplifier 117 and then fed to the A/D block 101 in FIG. 1.

The lower part of FIG. 2 shows the main connections and the electrode pair selection control lines 109, 109' from the microprocessor 103 of FIG. 1 to analog multiplexers 111, 111'. Adaptor 118 reduces the main voltage from 230 V to 5 V and rectifies the output voltage. An electrolytic ISO DC/DC converter 119, without direct connection, prevents ing noise and short-circuiting in case one of the circuits is shorted. Power supply 120 serves those circuits that are noise-protected.

As already mentioned, optocouplers 110 bridge screening barrier 121 and transmit the electrode selection commands from the microprocessor 103 of FIG. 1.

Not shown in FIG. 2 are the microprocessor 103 and the monitor 106 of FIG. 1. The information obtained from the signal analysis in block 105 and stored in the memory bank of the microprocessor is used by the system to identify the eggs not containing a living embryo and to facilitate the discarding thereof, as will be described further below.

Figure 3:
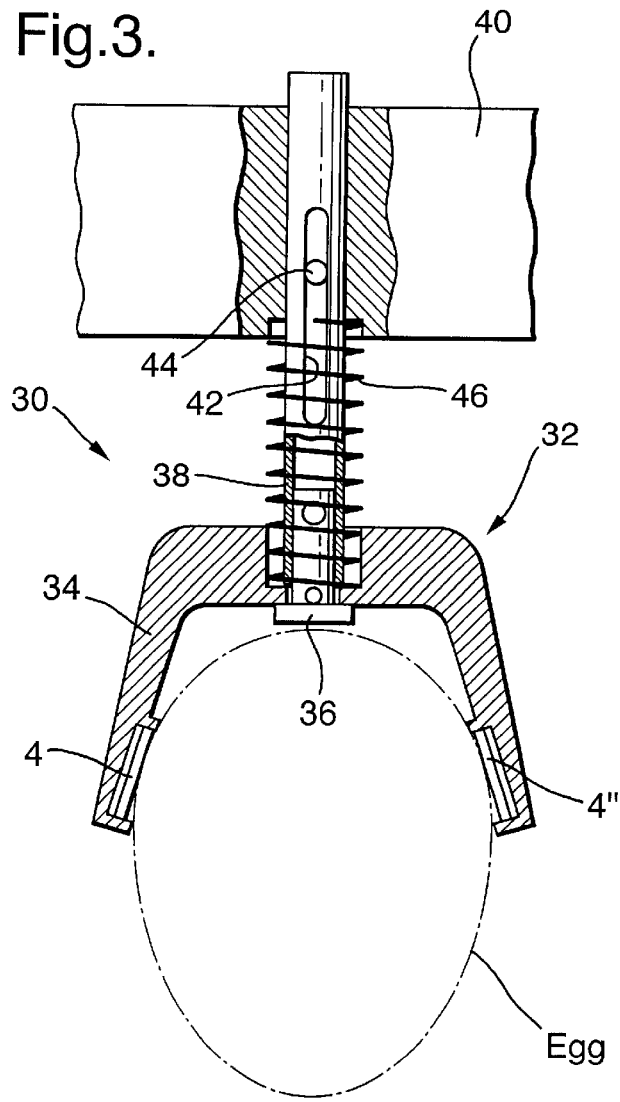
FIG. 3 is a cross-sectional elevational view along plane III—III of FIG. 4, of a detector head according to the present invention.
Figure 4:
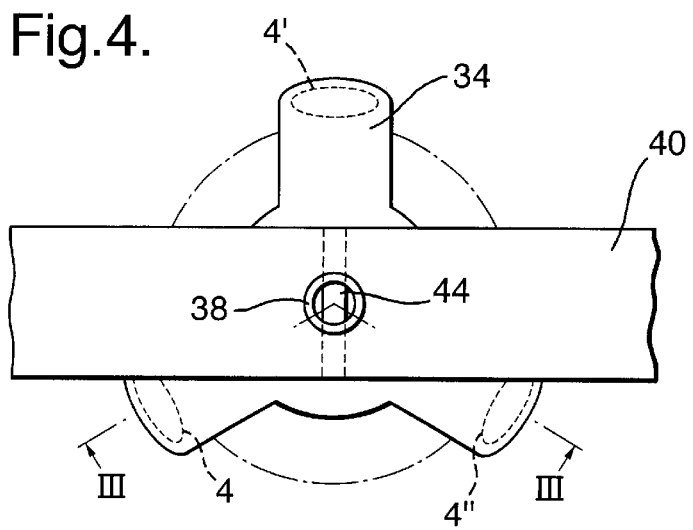
FIG. 4 is a top view of the three-pronged electrode holders of the detector head of FIG. 3.

A detector head 101, illustrated in FIGS. 3 and 4, is seen to comprise a three-pronged electrode holder 122 whose arms 123 (FIG. 3) have been swung into the paper plane for simplicity. To the end of each arm 123 there is attached one of the electrodes 107, 107', 107". These electrodes advantageously consist of a silver-silver chloride alloy and have a thickness of about 0.6 mm. Their electrical characteristics are:

| | |
|---|---|
| DC offset voltage (bios potential) | 180 μV |
| drift (at constant temperature) | 25 μV/h |
| noise (0.1–1 kHz, with 60 Hz filtered out) | 1 μVP-P |
| polarization (counter EMF) | 2–4 μV at 0.1 μA. |

These electrodes are intended to receive the weak electrical signals originating in the active heart of the living embryo.

Fixedly attached to holder 122 is a plug 124, over which is slipped, and to which is pinned, a tubular member 125. The tubular member is slidingly guided in a crossbeam 126 which, in this particular embodiment, carries another four detector heads 101, i.e., five heads altogether.

An elongated slot 127 passing through a tubular member 125 cooperates with a pin 128 seated in crossbeam 126 and permits the detector head 101 one degree of freedom in translation only, i.e., the head can move up and down, but it cannot rotate about the axis of the tubular member. The Pin also limits the up-and-down stroke of the detector head.

A helical spring 129 provides the contact pressure required for electrodes 107, 107', 107" to function properly. There are ten crossbeams 126 per testing unit 130 and 131 of FIG. 5, as will become apparent in conjunction with FIG. 5. When the crossbeams are lowered towards the eggs, the spring 129 is deformed in compression as soon as the electrodes touch the eggshell, providing adequate pressure without endangering the eggshell. The eggs to be assayed are arrayed in special trays 133 of FIG. 5, to be discussed further below, which ensure that half of the eggs are in alignment with the array of detector heads 101.

FIG. 4 is a top view of a detector head 101, showing the arms 123 of a three-pronged electrode holder 122, which arms are angularly spaced by 120°. Adjacent detector heads are mutually offset angularly by 60°, so that their arms will not interfere with one another.

FIG. 5 shows the work stations of the system. For greater clarity, the respective slides of the testing units 130 and 131 and the egg separating unit 132 have been removed so that only uprights 134, 134', 134" are shown along which these slides can move.

Figure 7:
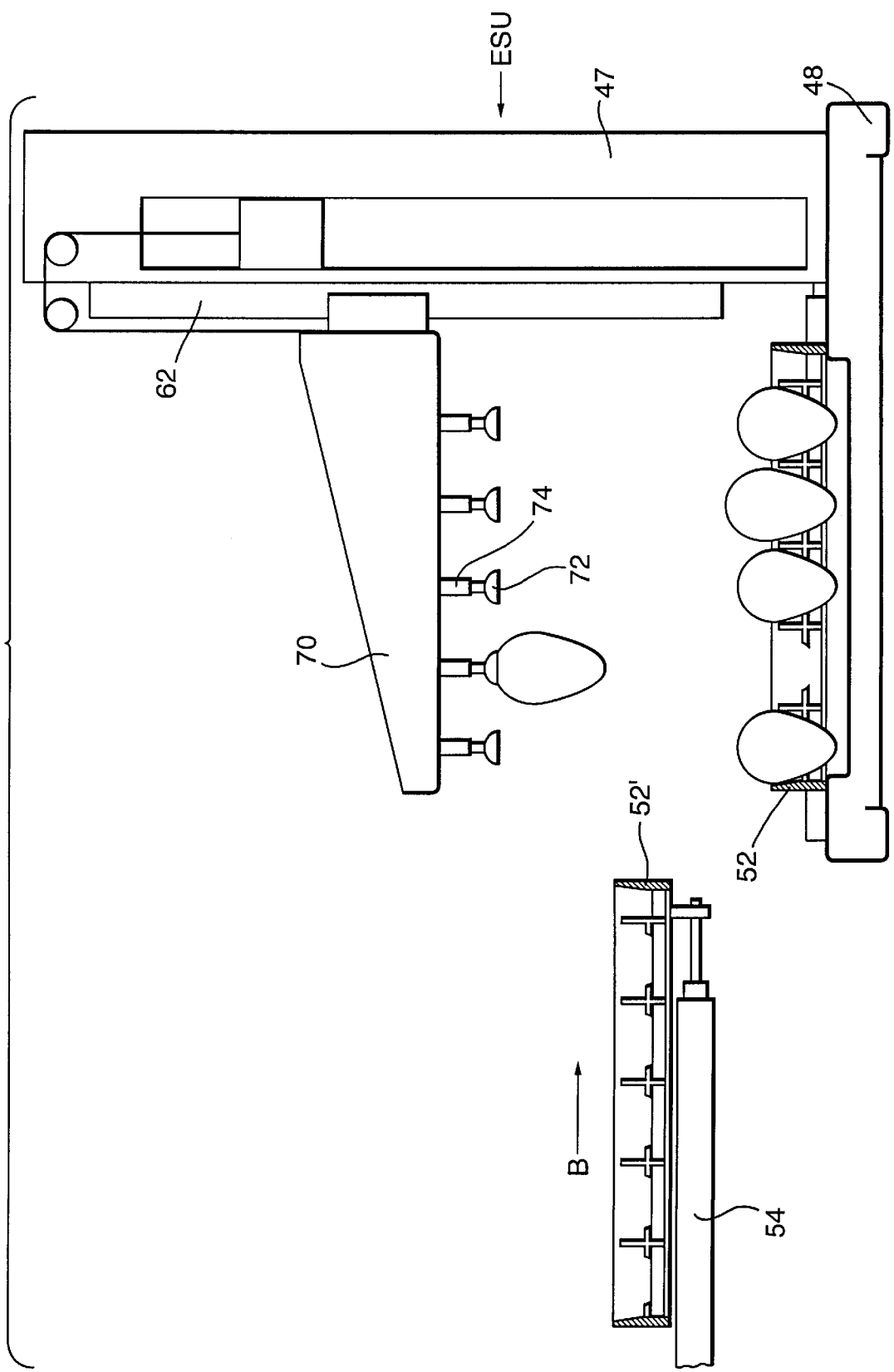
FIG. 7 is a schematic side view of a unit for separating the eggs found to be non-incubatable.

There is a bench or table 135. Along the bench moves a conveyor belt 136 that carries three trays 133 of the type shown in greater detail in FIG. 6. A fourth empty tray 133', the purpose of which will become apparent further below, is located adjacent to and above the plane of the conveyor belt, as seen in FIG. 7. The trays of this embodiment are designed to accommodate 100 eggs each, and those trays that are located on the conveyor belt are all full of eggs. The markings on every other column of eggs of the trays at the testing units 130 and 131 symbolize the electrode holders 122 of the detector heads 101, the rest of which have been removed with the respective slides. It can be seen that the electrode holders of the testing unit 130 make contact only with the eggs in every odd-numbered column of eggs (counting from the right), while the electrode holders of the testing unit 131 make contact only with the eggs in every even-numbered column of eggs. The small circles within the eggs of the tray at the egg-separating unit 132 symbolize the suction cups 137 of FIG. 7. In a sequence to be explained further below, the non-incubatable eggs are separated from the incubatable ones by means of the suction cups. The empty tray 133' is used to remove the non-incubatable eggs, in a manner to be described in conjunction with FIG. 7.

Telescoping beams 138 mounted on base plates 139 support the egg removal tray 133'. This tray is capable of moving in the direction of double arrow A by mechanical or pneumatic means. A more detailed description of this movement will also be given in conjunction with FIG. 7.

FIG. 6 is a top view of an egg tray 133. In this embodiment, the egg tray consists of 100 largely hexagonal cells 140, arranged in a honeycomb pattern in 20 columns having 5 cells each. Each column is offset from its adjacent column by half the pitch, as dictated by the pattern. Each cell is also provided with a number of radially directed lugs 141 which, in cooperation with the walls of each cell, serve to hold the eggs to be tested in a substantially vertical position.

FIG. 7 shows the egg separating unit 132 briefly discussed above in conjunction with FIG. 5. Apart from the bench 135, the upright 134", and the tray 133, a slide 142 is seen riding along a guideway 143. The slide is raisable and lowerable either manually or electrically. The slide carries 100 spring-loaded suction cups 137, telescopingly mounted in stems 144. As indicated in FIG. 5, the suction cups 137 are aligned with the centers of cells 140, i.e., with the eggs seated in these cells. Each suction cup is connected to a vacuum manifold via its own solenoid valve (not shown), which is controlled by the microprocessor 103 of FIG. 1 of the system.

The egg shown being suspended from one of the suction cups is first found non-incubatable by the testing unit 130 or 131. When the relevant tray 133 reaches the egg separating unit 132, the slide 142 is lowered so that the suction cups 137 make contact with the eggs, and a command is issued by the microprocessor 103 of FIG. 1 to the solenoid valve for the suction cup which is in contact with the non-incubatable egg. This suction cup is then lifted off the tray when the slide is raised. The egg removal tray 133' is then pushed forward in the direction of arrow B until it is aligned with lower tray 133. The slide is then lowered until the rejected egg enters the appropriate cell 140 in the egg removal tray. At this moment, a command from the microprocessor breaks the vacuum, causing the egg to be released by the suction cup. After this, the egg removal tray is withdrawn and the non-incubatable eggs are discarded.

Similarly, in the testing units 130 and 131, there is a bench, upright with its guideway, along which a slide can move, balanced by a counterweight. The slide carries the detector heads 101 of FIGS. 3 and 4, as well as a Faraday cage. The Faraday cage accommodates all of the electronic components belonging to block 100 in FIG. 1 and detailed in FIG. 2. The slide, located about an egg tray 133 of FIG. 5, can be raised and lowered either manually or electrically, like the slide 142 of FIG. 7. The system according to the invention can simultaneously process eggs of different sizes, as the springs 129 of FIG. 3 will compensate for any such differences.

Thus, apart from the electronics discussed earlier, the system according to the present invention comprises a plurality of detector heads 101 equipped with electrodes 107, 107', 107"; slides carrying these heads and movable vertically up and down; trays 133 accommodating, in well-defined arrays, the eggs to be examined; and a slide 142 carrying suction cups for removing the eggs found not to contain a living embryo.

The sequence preceding the above-described egg separation and disposal will now be described. Assuming that the conveyor belt 136 of FIG. 5 is empty of trays 133, as is the case, e.g., at the beginning of the working day, a full tray is placed on the conveyor belt in front of testing unit 130. The slide is then lowered until the detector heads 101 of FIGS. 3 and 4 make contact with the eggs in columns 1, 3, 5 . . . 19. After this, the electronic part of the system described above is switched on and, after some seconds, determines which eggs in the array of odd-numbered columns are non-incubatable. The results of the above-described analysis are stored in the memory bank of the microprocessor 103 of FIG. 1 and the conveyor belt moves one step, after which the station in front of the testing unit 130 is vacant and the station in front of the testing unit 131 is occupied by the tray in which the eggs in the odd-numbered columns have just been tested. The station in front of the egg separation unit 132 is still vacant.

A second full tray 133 is then placed in front of the testing unit 130 and the eggs therein are analyzed, with the results again being stored. At the same time, the detector heads 101 of the slide of the testing unit 131 are brought into contact with the eggs in columns 2, 4, 6 . . . 20. These eggs are analyzed and the results are stored. The conveyor belt 136 again advances by one step. After this, the station in front of the testing unit 130 is vacant, the station in front of the testing unit 131 is occupied by the second tray with the eggs of the odd-numbered columns of which have just been tested, and the station in front of egg separation unit 132 is now occupied by the first tray, whose full complement of eggs, i.e., all odd-numbered and all even-numbered columns of eggs, have been analyzed in the previous two steps. At this point, the microprocessor 103 of FIG. 1 retrieves the stored results of the analysis, initiating the above-described egg separation and discarding sequence. Simultaneously, a new full tray is placed on the conveyor belt in front of the testing unit 130 and the cycle repeats itself.

Figure 8:
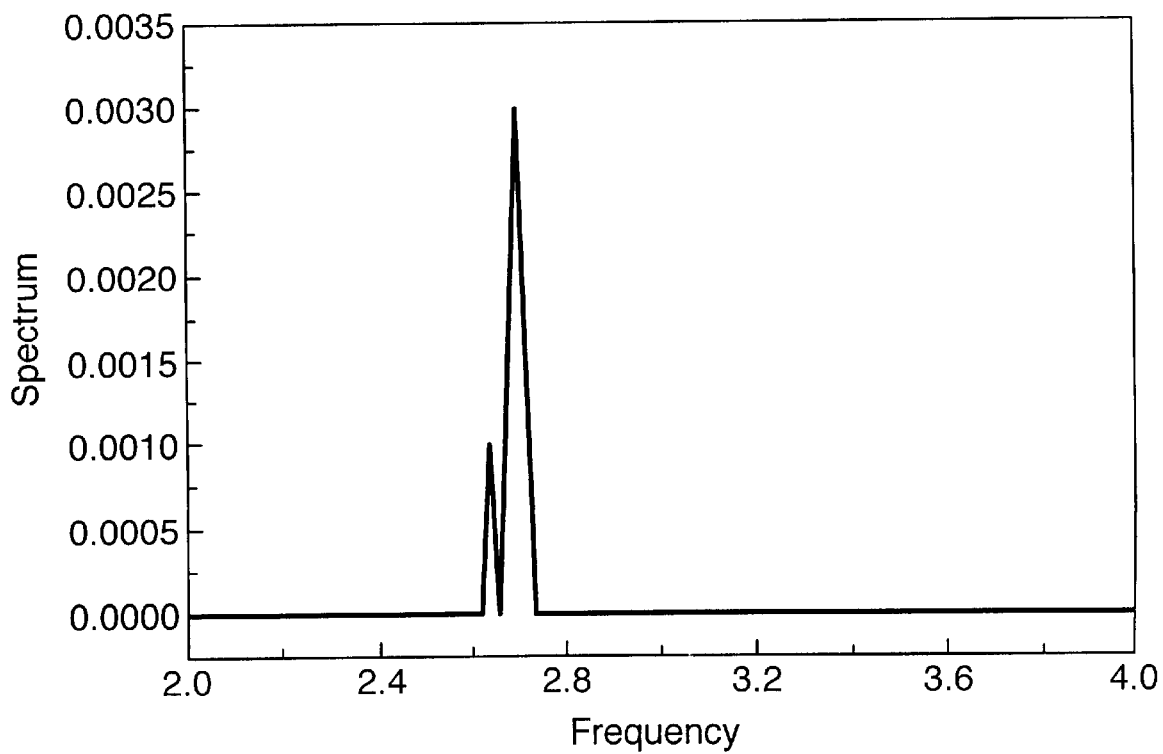
FIG. 8 is a characteristic curve of embryo heartbeats.

The present method can be utilized not only to determine fertilization of eggs, but also to distinguish between the sexes of the embryos. Referring to FIG. 8, there is shown a frequency vs amplitude curve of embryo heart beat pulses measured by the method and apparatus of the present invention. It can be clearly seen that beats measured at about 2.7 Hz, which is about 160 beats per minute, exhibit two peaks, at a difference of between about 0.5–0.8 Hz, indicating pulses of different sexes of the embryos.

It is also possible to implement the method of the present invention using a thermal camera instead of the electrodes.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method for verification of the presence of a living embryo in an incubating poultry egg, comprising the steps of:

causing at least two electrodes to make conductive contact with the outside surface of the shell of said egg;

amplifying any analog signal received via two of said electrodes;

analyzing the amplified said signal using a program executable by a microprocessor to establish whether said signal originated in cardiac activity of said living embryo, and using such analysis to provide information confirming or negating the presence of a living embryo in said egg.

2. The method of claim 1, further comprising the step of selecting from said electrodes a pair of electrodes that yields a strongest said analog signal.

3. The method of claim 1, further comprising the step of filtering an amplified said analog signal to reduce extraneous noise superposed thereon.

4. The method of claim 3, further comprising the step of converting an amplified and filtered said analog signal into a digital signal to be analyzed by said program upon execution by said microprocessor.

5. The method of claim 1, further comprising the step of storing said information in a memory bank associated with said microprocessor.

6. The method of claim 5, further comprising the step of retrieving said information from said memory bank and using said information to facilitate separation of eggs for which said information negates presence of a living embryo from eggs for which presence of a living embryo has been confirmed.

7. The method of claim 1, further comprising the step of converting said information into a visual display.

8. A system for verification of the presence of living embryos in incubating poultry eggs, comprising:

an array of detector heads, each of said heads including at least two electrodes adapted to make contact with a surface of a shell of one of said eggs;

a microprocessor responsive to a signal received by said two electrodes, and adapted to establish presence or absence of cardiac activity of a live embryo from said signal; and means, coupled to said microprocessor for facilitating separation of eggs found lacking such presence from eggs in which such presence has been confirmed.

9. The system of claim 8, further comprising filter means for reducing extraneous noise superposed on said signal.

10. The system of claim 8, further including an egg tray defining an array of cells into which eggs to be examined are insertable, small end pointing downward, and rest, said egg tray disposable in a defined position such that said array of cells is alignable with said array of detector heads.

11. The system of claim 10, further comprising an array of suction cups, congruent with said array of cells, mounted on a vertically translatable slide having a resting position in which said suction cups are remote from said eggs and having a working position in which said suction cups are in contact with said eggs.

12. The system of claim 11, wherein said suction cups are coupled to said microprocessor such that eggs found to be lacking presence of a living embryo are removed from said tray when said slide moves from said working position to said resting position.

13. The system of claim 12, further comprising means for removing and discarding eggs removed from said tray.

14. The system of claim 8, wherein each of said detector heads is provided with three electrodes spaced-apart angularly by 120°; and further including analog multiplex means for sampling a signal provided by said electrodes, coupled to said microprocessor, whereby from which three electrodes that pair of two electrodes which yields the strongest signal is selected by an analog multiplexer means controlled by said microprocessor, through a process of signal sampling.

15. The system of claim 8, wherein said detector heads are mounted on a vertically translatable slide having a resting position in which said electrodes are remote from said eggs, and having a working position in which said electrodes are in conductive contact with shells of said eggs.

16. The system of claim 8, further comprising an array of suction cups, congruent with said array of cells, mounted on a vertically translatable slide having a resting position in which said suction cups are remote from said eggs, and having a working position in which said suction cups are in contact with said eggs.

17. The system of claim 16, wherein said suction cups are coupled to said microprocessor such that eggs found to be lacking presence of a living embryo are removed from said tray when said slide moves from said working position to said resting position.

18. The system of claim 17, further comprising means for removing and discarding eggs removed from said tray.

* * * * *